(12) United States Patent
Breon et al.

(10) Patent No.: US 9,672,187 B2
(45) Date of Patent: Jun. 6, 2017

(54) SYSTEM AND METHOD FOR DIRECTING GUIDED WAVES THROUGH STRUCTURES

(71) Applicant: Electric Power Research Institute, Palo Alto, CA (US)

(72) Inventors: Luke Breon, Concord, NC (US); Michael J Quarry, Charlotte, NC (US); Joseph L. Rose, State College, PA (US); Ehsan Khajeh, Spring, TX (US)

(73) Assignees: ELECTRIC POWER RESEARCH INSTITUTE, Palo Alto, CA (US); The Penn State Research Foundation, University Park, PA (US)

( * ) Notice: Subject to any disclaimer, the term of this patent is extended or adjusted under 35 U.S.C. 154(b) by 1006 days.

(21) Appl. No.: 13/842,061

(22) Filed: Mar. 15, 2013

(65) Prior Publication Data
US 2014/0278193 A1 Sep. 18, 2014

(51) Int. Cl.
*G06F 15/00* (2006.01)
*G01M 7/02* (2006.01)
(Continued)

(52) U.S. Cl.
CPC ........... *G06F 15/00* (2013.01); *G01M 5/0025* (2013.01); *G01M 5/0066* (2013.01);
(Continued)

(58) Field of Classification Search
CPC ...... G06F 15/00; G01N 29/043; G01N 29/11; G01N 2291/0425; G01N 2291/2634;
(Continued)

(56) References Cited

U.S. PATENT DOCUMENTS

| | | | | |
|---|---|---|---|---|
| 5,469,743 A | * | 11/1995 | Zorn | G01N 29/27 73/620 |
| 2009/0078049 A1 | * | 3/2009 | Sinha | G01N 29/02 73/623 |
| 2015/0016682 A1 | * | 1/2015 | Levy | A61N 7/02 382/103 |

OTHER PUBLICATIONS

Jacob Owen Davies, Inspection of Pipes Using Low Frequency Focused Guided Waves, Apr. 2008, Department of Mechanical Engineering Imperial College London, pp. 1-205.*
(Continued)

*Primary Examiner* — Sujoy Kundu
*Assistant Examiner* — L. Anderson
(74) *Attorney, Agent, or Firm* — Dergosits & Noah LLP

(57) ABSTRACT

A non-destructive testing system includes directing guided wave energy to regions of interest in waveguides. Knowing the propagation paths taken by guided wave energy in complex waveguides can be used to intentionally insonify regions of interest. Additionally, knowledge of the propagation direction and location of an energy mode in a waveguide allows the calculation of the path previously taken by the energy mode. This information can be used for signal processing of guided wave inspection systems. The test system can have various sensor configurations including: a single transducer configured to direct or receive guided wave energy along a particular direction, a one-dimensional array or a two dimensional array of transducers. The transducers can operate independently to provide mutual phasing and amplitude adjusting to steer guided wave energy in a waveguide or determine the directionality of guided wave energy received by the sensors.

31 Claims, 9 Drawing Sheets

(51) Int. Cl.
  *G01N 29/07*  (2006.01)
  *G01M 5/00*  (2006.01)
  *G01N 29/04*  (2006.01)
  *G01N 29/11*  (2006.01)
  *G01N 29/36*  (2006.01)

(52) U.S. Cl.
  CPC ........... *G01N 29/043* (2013.01); *G01N 29/07* (2013.01); *G01N 29/11* (2013.01); *G01N 29/36* (2013.01); *G01N 2291/0425* (2013.01); *G01N 2291/2634* (2013.01); *G01N 2291/2638* (2013.01)

(58) Field of Classification Search
  CPC .......... G01N 2291/2638; G01N 29/07; G01M 5/0025; G01M 5/0066
  See application file for complete search history.

(56) References Cited

OTHER PUBLICATIONS

Alessandro Demma, The Interaction of Guided Waves With Discontinuities in Structures, Jan. 2003, Department of Mechanical Engineering Imperial College of Science, Technology and Medicine London, pp. 1-213.*

\* cited by examiner

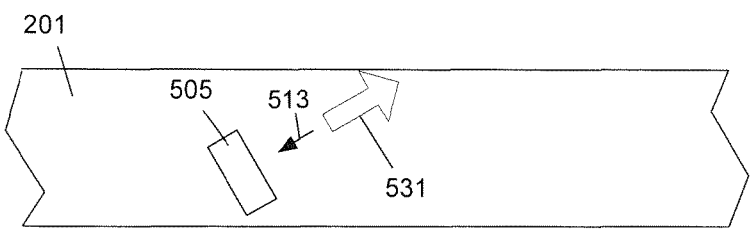
FIG. 7
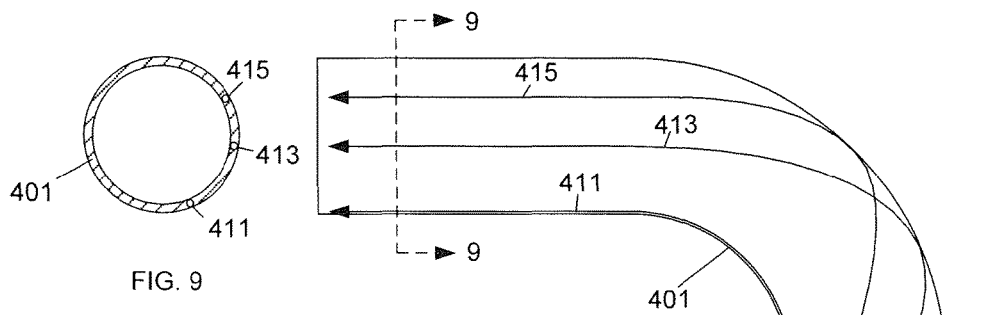
FIG. 9
FIG. 8
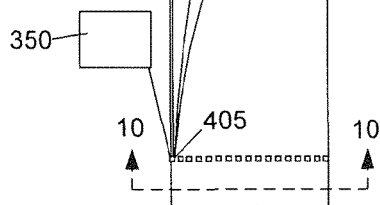
FIG. 10

SYSTEM AND METHOD FOR DIRECTING GUIDED WAVES THROUGH STRUCTURES

FIELD OF THE INVENTION

The present invention is directed towards guided wave operations in waveguides of signals through structures having complex or simple geometries. Plates, pipes, tubes, and rail are applications.

BACKGROUND

Guided wave testing is a method used for non-destructive evaluation. The method employs mechanical stress waves that propagate along a waveguide structure and are guided by the structures boundaries. Guided waves can typically travel tens of meters in these structures. Guided wave testing is used to inspect and screen many structures, particularly for the inspection of metallic pipelines. Pipes are used in hazardous applications such as fluid transportation systems for nuclear power plants, transmission and distribution of gas, refining of petroleum, and other hazardous material transportation systems. These piping systems often must change direction over the course of their paths to transport the contents to the desired location. Hence, there is often an important need to non-destructively inspect inaccessible regions where the guided wave must propagate around an elbow, bend, or other complex geometry. An ability to rapidly and reliably direct guided wave energy to regions of interest and focus guided wave energy at points of interest would greatly expand the functionality and practical implementation of guided wave systems for non-destructive structural testing.

SUMMARY OF THE INVENTION

The present invention is directed towards a non-destructive testing system that includes directing guided wave energy to regions of interest in a structure. By applying mathematical modeling described herein to the geometry of the structure, the inventive system can very quickly predict the propagation paths taken by guided wave energy through the structure. This method can be applied to structures having simple or complex geometries especially those having bend sections. The method can also be applied to parametrically defined or digitally defined geometries. Based upon the geometric mathematical modeling and analysis, a computer can determine test parameters that can be used to prescribe the directions, phases and amplitudes of wave energy emitted by one or more guided wave transducers coupled to the test structure. These parameters can cause the transducers to emit test signals that can insonify specific regions of interest in a structure.

If the wave energy contacts a feature in the structure, reflected wave energy can be transmitted back through the structure to the transducers. The transducers can detect the reflected wave energy and a processor can analyze the reflected signals. In an embodiment, it is possible to determine the axial and circumferential location of the reflective feature based upon the travel time of the reflected wave energy and the predicted path of the reflected wave energy.

In an embodiment, the controller can determine, control, and record the propagation direction and location of an energy mode in a waveguide. This information can allow the calculation of the insonification paths previously taken by a received energy mode and can be used for signal processing of guided wave inspection systems. A structure having a matching geometry will have the same mathematical modeling. Thus, a database of guided wave input parameter data can be usefully applied to any matching physical structures.

In different embodiments, the inventive test system can have various transducer configurations including: a single transducer configured to direct or receive guided wave energy along a particular direction, a one-dimensional array or a two dimensional array of transducers. The transducers can operate independently to provide mutual phasing and amplitude adjusting to steer guided wave energy in a waveguide or determine the directionality of guided wave energy received by the sensors.

BRIEF DESCRIPTION OF THE DRAWINGS

FIG. 7 illustrates an embodiment of a directional guided wave transducer on a pipe;

FIG. 8 illustrates a top view of a pipe structure with different wave energies transmitted through the pipe structure;

FIGS. 9 and 10 illustrate sections views of the pipe structure illustrated in FIG. 8;

DETAILED DESCRIPTION

Figure 1:
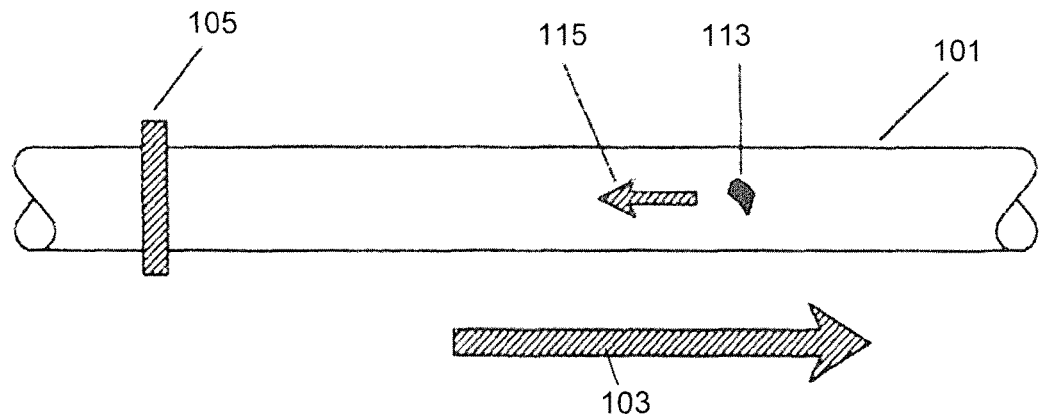
FIG. 1 illustrates a pipe with a guided wave energy test apparatus.

It is an objective of this present method to provide means for accurately directing guided wave energy to regions of interest in a waveguide structure having a complex or simple geometry. In an embodiment with reference to FIG. 1, one or more transducers 105 can be mounted on a portion of a pipe structure 101. The one or more transducers 105 can be actuated to transmit pulses or bursts of wave energy 103 that travel through the structure 101 for non-destructive testing. In this example, the wave energy 103 is traveling right through a pipe structure 101. If the wave energy contacts a feature or a defect 113 in the structure, the wave energy can reflect back as reflected energy 115 from the defect 113 towards the one or more transducers 105. The transducers 105 can detect the reflected wave energy 115 and process the detected reflected signals. A processor may determine that the reflected signals are from a defect 113 in the structure 101. Examples of features that can cause the wave energy 103 to reflect back include: cracks, corrosion, welds, holes, coating delaminations, ground penetrations, wall thinning and other geometric features. In other embodiments, the inventive system and method can be used for non-destructive testing of structures having complex geometries.

In an embodiment, this inventive method can be used with existing guided wave inspection hardware including existing sensor and transducer systems capable of directing and/or receiving a guided wave of one or more of any mode type or combination of mode types in a desired direction on a waveguide structure being tested. The inventive method can be performed with systems that can include various combinations of components. For example, in an embodiment, the system may include a single transducer or a one-dimensional array of transducers that are equally spaced or non-equally spaced from each other. In other embodiments, the system components can include a two-dimensional array of equally spaced or non-equally spaced transducers.

The energy wave signals emitted by the transducers can be transmitted through any structures having a waveguide construction. A hollow metal pipe is a suitable waveguide structure because it can be used to transmit ultrasonic energy waves. Guided waves can generally propagate in all directions with respect to the surface of a waveguide. Thus, these energy waves generally lose their intensity proportionally to the distance traveled due to geometric dispersion. For example, at a distance R from the transducer, or source, the power of the wave energy is the power emitted by the transducer divided by R. In contrast, wave energy transmitted through a straight or curved pipe waveguide is effectively confined to propagate in one dimension, so that geometric dispersion does not cause a non-dispersive guided wave to lose significant power while propagating. Wave energy is confined inside the waveguide due to reflection from the waveguide wall. Other suitable waveguide structures include structures like plates, rails, beams, and rods.

Figure 2:
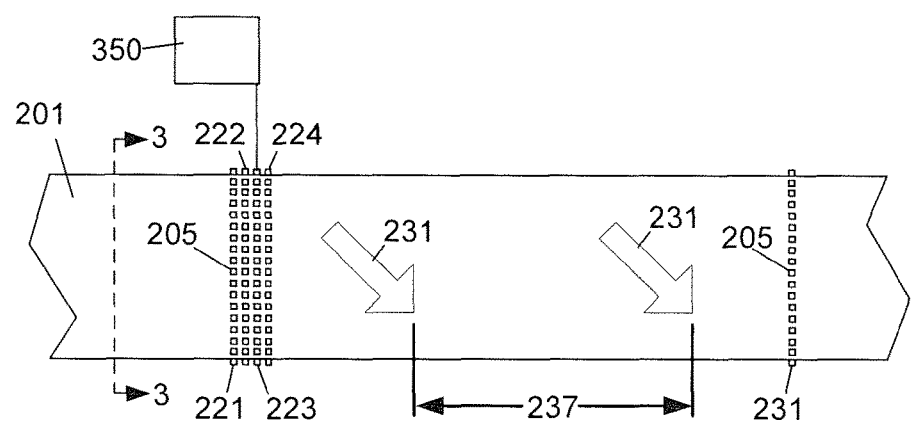
FIG. 2 illustrates a pipe with a guided wave energy test apparatus having a two-dimensional array of transducers.
Figure 3:
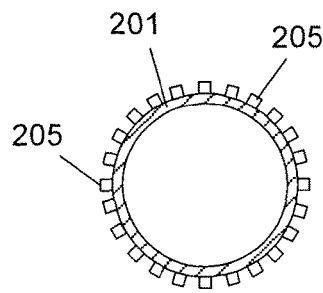
FIG. 3 illustrates a cross section of a pipe with a guided wave energy test apparatus having a two-dimensional array of transducers with independent axial positions.

In an embodiment the test system can include a guided wave system having a computer or a controller that is used to control a two-dimensional array of equally spaced transducers on a pipeline test structure with a separate channel for each sensor or sensor group in the array. An example of a two-dimensional array transducer configuration is illustrated in FIG. 2. In this embodiment, the structure being tested includes a cylindrical pipe 201 and the transducers 205 are arranged in a two-dimensional array with the transducers 205 equally spaced in alignment around the pipe 201. FIG. 3 is a cross sectional view of the pipe 201 showing the transducers 205 around the pipe 201.

In this embodiment, the transducers 205 can each be oriented normal to the pipe 201 surface and arranged into a plurality of rings 221, 222, 223, 224 around the pipe. Each ring 221, 222, 223, 224 can have the same number of transducers 205. The rings 221, 222, 223, 224 can be equally spaced axially from each other and the transducers 205 can cover mutually identical circumferential footprints on the pipe surface 201. Each transducer 205 can belong to a particular ring 221 and each transducer 205 can share a common circumferential location on the pipe 101 with corresponding transducers 205 on other rings 222, 223, 224 in this configuration.

In an embodiment, the transducers 205 in the rings 221, 222, 223, 224 can be controlled by a computer to enable guided wave energy 231 to be sent in a controlled direction along the pipe 201 in a helical path with the pitch 237 of the helix controlled by the timing and phasing of the actuation of the transducers 205. This pitch may range from zero, representing a purely circumferentially oriented guided wave, to infinity, representing a purely axially oriented guided wave. This construction also allows for the determination of the direction taken by guided wave energy 231 impinging on the sensor array by processing the time and phase differences of the wave as received by each transducer 205 in the array.

In an embodiment making use of multiple transducers, time and phase delays are applied to the transducers 205 in each ring 221, 222, 223, 224 to allow for guided wave energy steering and unwanted mode cancellation from each ring 221, 222, 223, 224 of transducers 205. This is effected by having the transducers 205 be coupled to a controller 350 which can transmit individual control signals to each of the transducers 205. The controller 350 can transmit control signals to each of the transducers 205 to emit pulses of differing amplitudes and phases and different timing. By precisely coordinating the wave energy emissions 231 from the transducers 205, the system can control the directions of the wave energy signals transmitted through the pipe structure 201.

In an embodiment, it can be important for the transducers to only transmit the guided wave energy in one direction through the pipe 101 to avoid multiple reflected signal interference. In order to perform this task, coordinated actuation of the transducers can be required. When the transducers 105 are actuated, they can emit wave energy through the pipe 201 both towards the right and left from the rings 221, 222, 223, 224. However, if transducers 205 in other rings, such as 223 and 224 are controlled to emit pulses with correctly designed phase and or time delays, the net wave energy emitted by the rings 223, 224 can be in one direction through the pipe 101. For example, the transducers 205 in ring 224 will generally emit wave energy which propagates through the pipe 201 in the left and right directions. As the wave energy travels in the left direction, the transducers 205 in ring 223 can be actuated to emit a wave energy having a phase and or time delay that negates the wave energy passing underneath the transducers 205 in ring 223. The summation of the wave energy caused by the transducers 205 in ring 223 and the wave energy caused by the transducers 205 in ring 224 will sum to zero for the energy traveling to the left, but not for the energy traveling to the right.

In the example described above, the wave energy cancellation can be performed by two adjacent rings 223, 224. However, in other embodiments, any two transducers 205 from any two separate rings 221, 222, 223, 224 can be used to cancel wave energy traveling along one direction that is collinear with the two transducers 205. For this example, a first transducer 205 transmits energy in both (or, depending on the transducer 205 being used, all directions). A second transducer 205 can introduce the negative of the energy that passes under the first transducer 205. Because wave physics are such that wave energy can be combined, a first wave plus a second wave that is a negative of the first wave will sum to zero. The net result of the first wave from the first transducer 205 and the second wave from the second transducer 205 can be no energy after the second transducer 205 fires. Note that this wave cancellation may only apply to the first wave energy that started from the first transducer 205 and passed directly under the second transducer 205. Waves moving in other directions will not be canceled, and the two waves introduced by each respective transducer 205 may generally be combined to produce non-zero values in directions other than the direction from the first transducer to fire to the second transducer to fire.

The examples described above are only some of the wave emission combinations that are possible. By coordinating the wave energy timing, the opposite wave energy from ring 223 can cancel out the wave energy moving left from ring 224. Thus, only the wave energy remaining in the pipe 201 is travelling right from ring 224.

Figure 4:
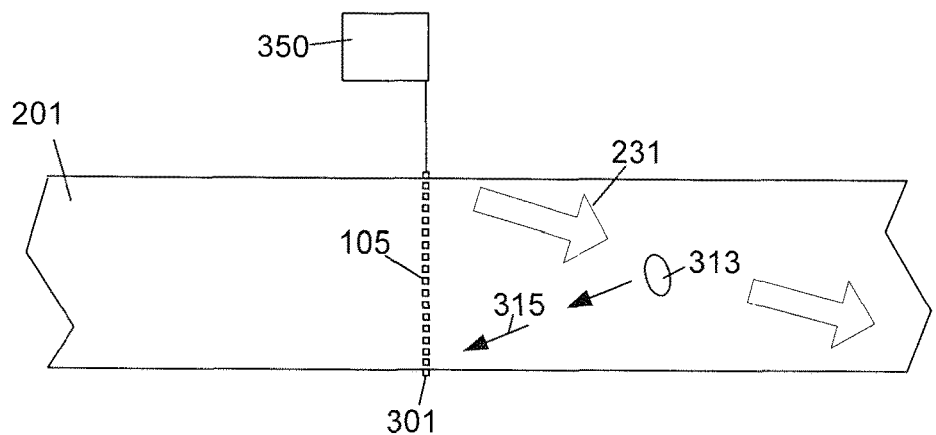
FIG. 4 illustrates a pipe with a guided wave energy test apparatus having a one-dimensional array of transducers.

With reference to FIG. 4, another embodiment includes a similar transducer array 301 for inspecting pipes comprised of a one-dimensional array 301 of transducers 205. The array 301 can be coupled to a controller 350 which can control signal inputs to the transducers and receive signals back from the transducers. In this embodiment, the transducers 205 can be arranged around the pipe 201 as described above, but in only a single ring array 301. Guided wave energy 231 can be introduced into the waveguide and directed through the pipe 201 as described above. The one-dimensional array 301 of transducers 205 is used to transmit and receive wave energy. For example, the one-dimensional array 301 can emit wave energy 231 signals through the pipe 201. The wave energy 231 signals can reflect off of one or more features on the pipe 201 and reflect back a group of wave energy signals 315 to the one-dimensional array 301.

The signals received by the transducers 305 can be transmitted to and analyzed by the controller 350. The reflected signals can be analyzed for position, phase, time and distance traveled. The controller 350 can then determine the location of the defect 313 based upon the reflected signals. The signals from the reflected wave energy 315 can be analyzed by the controller 350 to determine the location of the defect 313 based upon the wave energy 313 velocity and the time between signal transmission and the receipt of the reflected signal. The position of the defect 313 may be determined by knowing the angle of the helical path of the wave energy 231.

Figure 5:
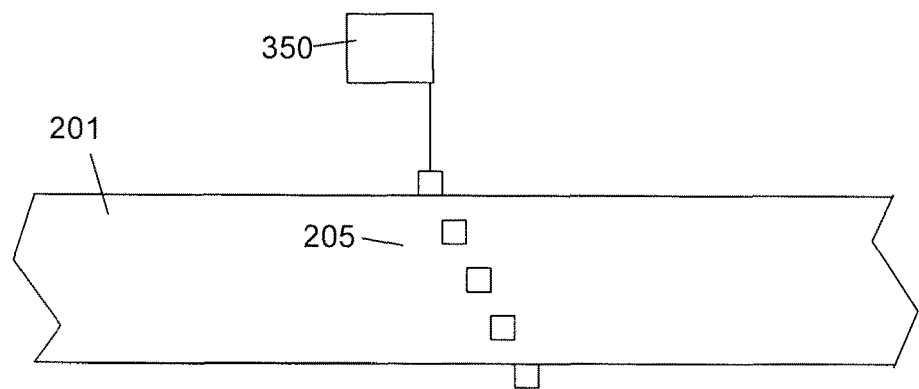
FIGS. 5 and 6 illustrate embodiments of a pipe with a guided wave energy test apparatus having a two-dimensional array of non-equally spaced transducers.
Figure 6:
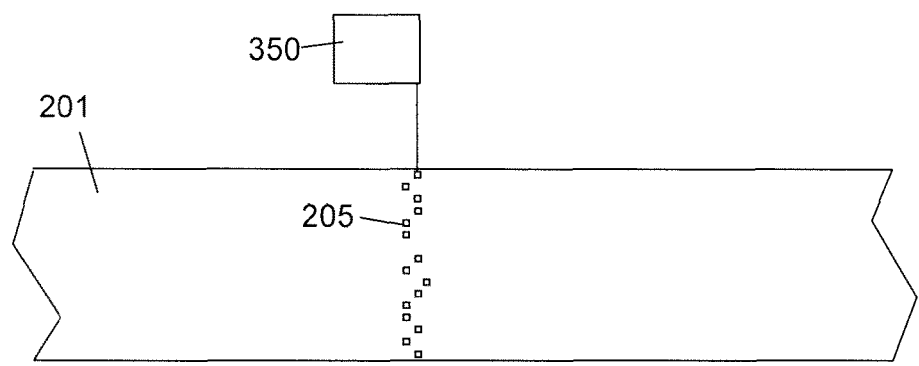

In other embodiments, various other transducer configurations are possible. With reference to FIG. 5, in another embodiment, a single one-dimensional array of equally spaced sensors for inspecting pipes is used with the inventive method. However, rather than belonging to a ring having a footprint contained entirely at a single axial location on the pipe, some or all of the transducers 205 are at mutually differing axial locations along a portion of the pipe 201. With reference to FIG. 6, an embodiment is illustrated with a two-dimensional array of non-equally spaced transducers 205 around a pipe 201. Signals can be emitted and received by the transducers 205 as described above.

The inventive system and method should include some form of a transducer or transducer array that is capable of generating and receiving a directional wave in any selected direction. The transducer arrays described in this application are intended to generate and receive a directional wave in any selected direction. There are various possible methods for steering the wave energy emitted by the transducer(s) through waveguide structures having complex geometries being tested. These methods can be used to direct wave energy through both straight and curved portions of the structures being tested. For example, in an embodiment, comb transducers can be used to control the steering angle through the structure based upon the transducer geometry and frequency of the wave energy. Comb transducers may not employ phasing or individual time delays to steer the emitted wave energy.

In an embodiment, a one dimensional array of inline transducers as shown in FIG. 4 can be used to steer wave energy through the waveguide structure being tested. The transducers in the array can be capable of individual actuation with programmable amplitudes as well as programmable time and phase delays. This array of transducers can be used to steer energy waves of any frequency to any desired angle by adjusting individual time and phase delays between the various transducers in the array. This configuration may require a minimum number of transducers around a circumference of the test structure and the transducers may need to be spaced appropriately from each other.

In an embodiment, a two-dimensional array of inline transducers can be used to steer the wave energy as shown in FIG. 2. The array of transducers can be capable of individual actuation with programmable time and phase delays. A two-dimensional array of transducers can function like the one dimensional array of transducers. However, the two-dimensional array can provide a more powerful wave energy output as well as wave energy cancellation. The additional transducers and more individually programmable channels improve the versatility and power output from the transducer array.

In other embodiments, a one-dimensional array of staggered transducers (shown in FIG. 5) or a two-dimensional array of staggered sensors (shown in FIG. 6) can be used to steer the wave energy through complex geometries. The locations of the staggered transducers can be strategically spaced to optimize particular steering angles of emitted wave energy. The locations of the transducers can also be optimized for receiving reflected wave energy to bias the received energy to preferentially enhance the reception of energy impinging on the sensor from particular reflected angles of interest while being less sensitive to reflected wave energy traveling at other angles; essentially acting a filter.

Wave energy steering can also be performed by a directional transducer or array of directional transducers. A directional transducer as shown in FIG. 7 is capable of generating energy in a single direction with a single transducer. The energy emitted by the directional transducer can go both in the forward direction and backwards direction. The use of the directional transducer may be similar to the array of staggered transducers, or may be used as non-fixed transducers that are placed on a waveguide structure and rotated dynamically as needed to excite energy in any desired direction. The directional transducer can be similar to the comb transducer in that there are no phase delays unless it is used in the context of an array and time delays are effected by the geometry of the directional transducer. Unlike the comb transducer, the frequency does not change the propagation direction of wave energy emitted by the directional transducer. The directional control of the wave energy from the transducers has been described by embodiments that coordinate an array of transducers. This directional control has also been described by embodiments that do not require coordinated time and phase delays in order to introduce guided wave energy in a desired direction. For example, with reference to FIG. 7, a transducer 505 can be positioned on the waveguide structure 201 at an angle so that wave energy emitted from the transducer 505 is also at this angle. The wave energy 513 from the transducer 505 can then travel in a helical manner around and along the pipe structure 201. The directional transducer 505 may be used to excite directional guided wave energy 531 and to receive guided wave energy 513 moving in the same or opposite direction and passing under the transducer 505. Because the transducer 505 is physically configured to produce a directional wave, time and phase delays are not required in order to direct the wave energy 513 in the desired direction through the pipe 201.

In an embodiment, the transducers can emit wave energies having very low ultrasonic frequencies, typically between 10~250 kHz. However, in other embodiments the inventive system and method can be operated at any frequency. Higher frequencies can be used in some cases, but the detection range of the testing signals with higher frequencies can be significantly reduced. There are numerous possible guided wave modes that can exist for a pipe geometry. However, these guided wave modes can be generally grouped into three categories: torsional, longitudinal and flexural modes. Various different types of transducers can be used to generate the guided wave modes in a structure including: piezo-electric transducers, magnetostrictive transducers, electro-mechanical acoustic transducers, angle beam transducers, comb transducers, electromagnetic acoustic transducers or any other transducers capable of generating and/or receiving a guided wave signal having one or more of any combination of modes. In additional embodiments, the inventive method can be used with guided waves of any mode type or combination of mode types including but not limited to: lamb modes, longitudinal modes, shear modes, torsional modes, shear horizontal and shear vertical modes, surface modes, and interface modes.

As discussed, the transducers can be mounted on the waveguide structure being tested. In an embodiment, the transducers can be mounted on one or more wedges, matching layers, face plates, or other coupling or backing media. In other embodiments, the transducers can be mounted directly onto the structure being tested with any connection mechanism, such as an adhesive or mechanical coupling. In an embodiment, two-dimensional rings of equi-spaced piezo-electric transducers can be used to generate the described torsional guided wave modes in the majority of test applications. In a preferred embodiment, the torsional wave mode can be used for non-destructive testing. The system can operate in a pulse-echo configuration where the array of transducers is used for both the excitation and detection of the signals, or in pitch-catch configuration in which mutually different sensor arrays are used for transmission and reception. At locations where there is a change of cross-section, a change in local stiffness of the pipe or other types of structural changes, an echo is generated and a wave will be reflected back towards the array of transducers. Based on the arrival time of the echoes, and the predicted speed of the wave mode at a particular frequency and the knowledge of how the particular wave energy will propagate, the axial distance and circumferential location of a change in the pipe in relation to the position of the transducer array can be accurately calculated. By knowing the geometric model of the structure being tested, the intended features can be distinguished from defects in the structure. Defects and features that can be detected by guided wave testing can include corrosion, cracking, pitting, holes, welds, supports, wall thinning, coating delaminations on the inner or outer surfaces of the pipe, contact points of the pipe with the ground and other geometric features such as branches, tees, elbows, flanges, vents and drains.

In some structures, the design of the cross-section of the structure can change and it is possible to compensate for these structural alterations. For example, guided wave testing can use a system of distance amplitude curves to correct for attenuation and amplitude drops when estimating the cross-section change from reflected wave energy. The distance amplitude curves can be calibrated against a series of reflected wave energy echoes with known signal amplitudes such as weld echoes.

A typical result of guided wave testing can be displayed in graphical manner with the reflection amplitude of the reflected wave energy shown against the distance from the transducer array position. The transducers are in fixed positions and the location of the feature or defect may be determined or estimated by the strength of the reflected energy waves as a function of time. In other embodiments, the inventive system can display the reflected energy wave information in alternative graphical formats.

Guided wave propagation can be determined in straight pipes. However, in more complex geometries like piping systems having elbows and other piping geometries, guided wave propagation can be more difficult to predict. Although Navier's equation can be solved for straight pipe, this equation cannot be solved analytically for geometric shapes that include pipe elbow bends. An embodiment of the inventive method is able to determine the trajectory of a guided wave mode through a complex structure given the initial conditions of the wave energy mode. These initial conditions involve the starting location of the wave energy mode and the initial direction of the wave energy mode. The location and direction of a guided wave energy mode can also be sampled at any time in a waveguide and from this information it is possible to determine the past trajectory of the wave mode. By knowing the trajectory of the guided wave modes in a waveguide structure given initial conditions, it is possible to design initial conditions for guided waves to send a wave energy mode to specific regions of interest in the structure for reliable insonification and testing.

In an embodiment, it is also possible for the inventive system to generate multiple instances of guided wave energy in the test structure. Each of the guided wave energies can start from mutually separate locations and each of these guided waves can have initial conditions such that each of the separate energy waves will converge at a specific predetermined point of interest simultaneously. This can allow multiple guided waves to focus energy at any point of interest in the structure.

The inventive method is based upon two characteristics of guided wave propagation. Guided waves may use a transverse resonance for wave propagation. In an embodiment the transverse resonance can be between the inner and outer surfaces of the structure. For example, in a pipe structure the wave energy resonance can be between the inner and outer diameter surfaces. Except for the case of impedance changes in the structure which will reflect or scatter a wave, once the guided wave energies are propagating through the waveguide structure being tested, the guided wave energy may not have motivation to change direction unless that motivation comes from the shape or geometry of the waveguide structure. Thus, a guided wave will propagate in a direction that appears to be straight forward from the point of view of the wave energy mode.

The transverse resonance pertains to the 2-dimensional cross-section lying between and being defined by the surface normals of, two opposing, bounding, surfaces of a waveguide, at a point coincident with the propagating energy. The guided wave energy propagates such that the wave energy is contained between the two bounding surfaces. Thus, when the two surfaces encounter a mutually similar curvature, the energy propagating between them must follow the curvature. In a pipe structure, the two opposing surfaces can be inner diameter and the outer diameter surfaces. For other structures, the two opposing resonance surfaces can be opposite sides of the structure such as a plate, rail, beam, etc.

It is the curvature of the structure that determines what direction appears to be straight ahead for propagating guided wave energy traveling through the structure. The curvature of a structure can be defined both by the concept of geodesics and from the surface normals of the structure. Guided wave energy will reflect from a surface symmetrically about the normal of the surface at the point of impingement. Tracing the path of consecutive boundary reflections will result in tracing a geodesic of the structure. Thus, geodesics of the bounding surfaces containing a guided wave describe the direction that appears to be straight ahead to a propagating guided wave.

Figure 14:
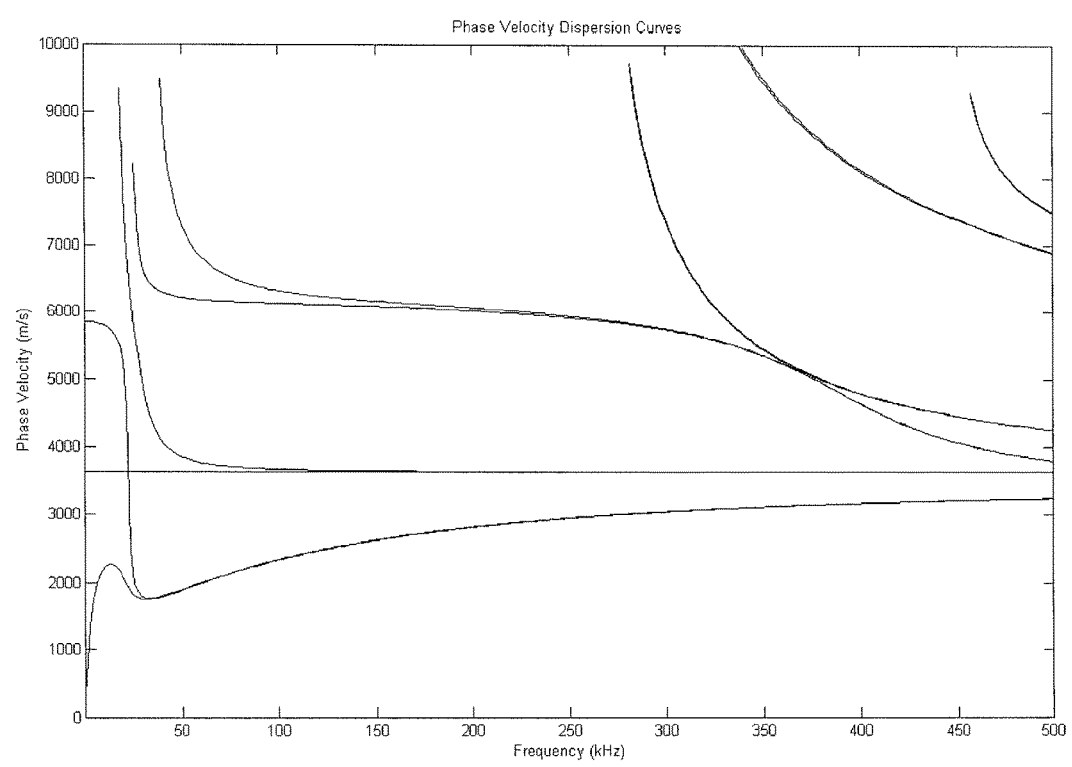
FIG. 14 illustrates a disperson curve graph for a straight pipe waveguide structure.

The acoustic properties of these wave modes are a function of the pipe geometry, the pipe material and the wave frequency. It is possible to predict the properties of the wave modes by using mathematical modeling which can be illustrated as graphical plots called dispersion curves. An example dispersion curve for a straight pipe is shown in FIG. 14. In other embodiments, any other waveguide can be similarly tested by predicting the acoustic properties of the wave modes and the pathway that appears straight to a propagating guided wave. Although the pathway can appear to be straight to the wave energy, the actual geometry of the structure being tested can be more complex than a simple straight pipe and may include one or more curved or bent sections. The mathematical modeling can represent the entire structure with curved and bent sections. The same process used for pipes can also be used for other structures having complex geometries.

In an embodiment, various equations can be used to mathematically model a test structure. The equations below following the notations of Zwillinger (1). ("CRC Standard Mathematical Tables and Formulae" 31$^{st}$ Edition, Chapman & Hall/CRC Press LLC. 2003.) A geodesic on a manifold M with an affine connection ∇ is a curve γ(t) such that the tangent vector to γ(t) is parallel along γ(t). This requires that the following equation be true:

$$\frac{\delta \dot{\gamma}}{\delta t} = 0 \tag{1}$$

In this equation, $\dot{\gamma}$ is the derivative with respect to t. The covariant derivative of γ can be obtained by expanding $\dot{\gamma}$ to a continuously differentiable vector field in an open set. Using local coordinates on M, the geodesic equation (1) can be written using the summation convention for surfaces with continuous spatial derivatives as:

$$\frac{d^2}{dt^2} = \Gamma^i_{jk} \frac{dx^j}{dt} \frac{dx^k}{dt} = 0 \tag{2}$$

In this equation, $x^j$ are the coordinates of the curve γ(t) and $\Gamma^i_{jk}$ are the Christoffel symbols of the connection ∇. The equation will have a unique solution for a given set of initial position and initial velocity. From the point of view of classical mechanics, geodesics can be thought of as trajectories of free particles in a manifold. The equation $$\frac{\delta \dot{\gamma}}{\delta t} = 0$$

means that the acceleration of the curve is purely normal to the surface. So, the surface can be thought of as a constraint surface, and the motion can be determined by the bending of the surface. This concept is used in general relativity for the study of particle motion where particles move on geodesics subjected to bending caused by the gravity. The gamma term from (2) is defined in equation (3):

$$\Gamma^i_{kl} = \frac{1}{2} g^{im}(g_{mk,l} + g_{ml,k} - g_{kl,m}) \tag{3}$$

the g-tensor is the metric of the surface and is defined in equation (4):

$$ds^2 = g_{ij} dx_i dx_j \tag{4}$$

Solving Equations 1 through 4 for a straight section of pipe will reveal that the geodesics of a pipe will result in a family of helices. However, working through Equations 1 through 4 for a pipe elbow leads to a pair of coupled partial differential equations that have no analytical solutions. These coupled partial differential equations can be solved numerically, however, given initial conditions.

In an embodiment, the trajectories of straight lines on general surfaces that may be defined by geometries with non-continuous spatial derivatives can also be obtained through another numerical method developed and demonstrated here. To determine the trajectory of a wave on a general surface that may be defined digitally, rather than parametrically, it is possible to iteratively solve for the solution given a previous known solution or a set of initial conditions by making use of the following equation:

$$S_i = T_i \cdot ds \tag{5}$$

The term $S_i$ in Equation (5) is the position vector in three dimensional space describing the displacement of the solution of the current iteration from the position of the previous solution. The ds term represents an appropriately small increment of distance. The term $T_i$ represents the direction of the velocity for the current iteration, and $T_i$ is defined by the equation below:

$$T_i = -N_{i-1} \times (N_{i-1} \times T_{i-1}) \tag{6}$$

Figure 17:
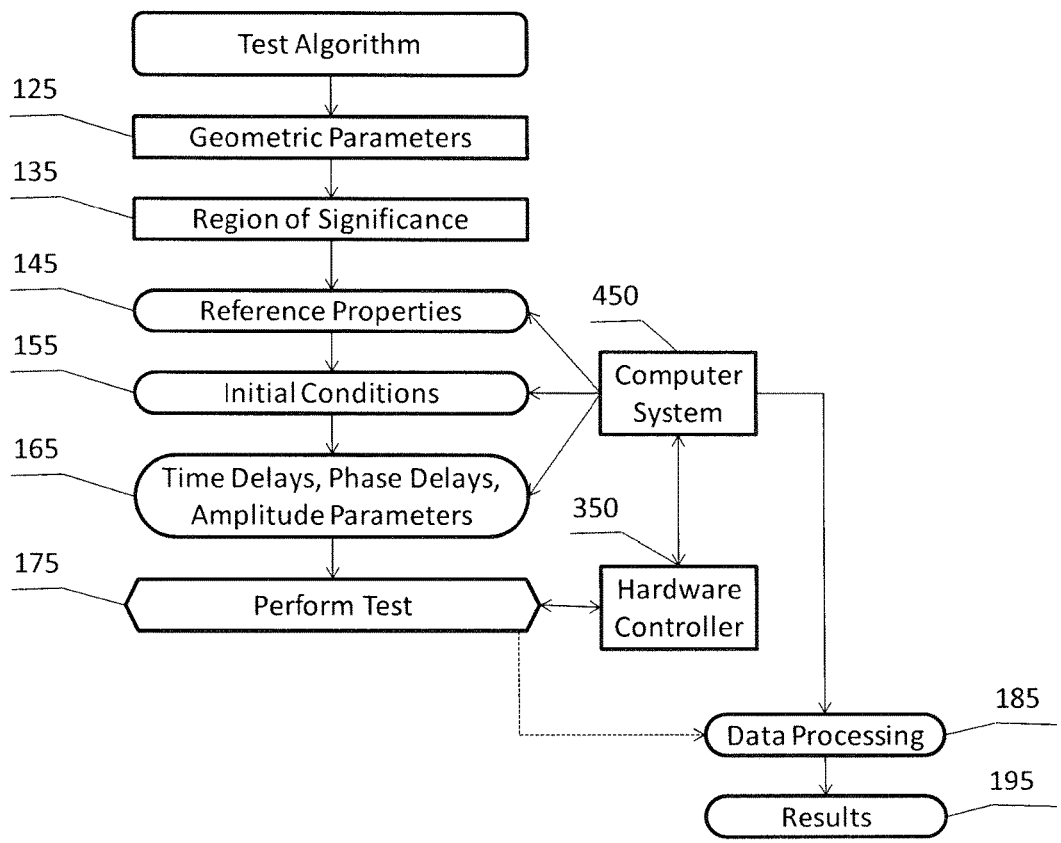
FIG. 17 illustrates a flow chart of an embodiment of a process for determining optimum waveguide excitation parameters.

In Equation (6), $N_i$ is the outward normal of the surface of relevance. Equations (5) and (6) will produce families of helical solutions along sections of straight pipe and will produce the same solutions on a pipe elbow as can be obtained from Equations (1) through Equation (4). Both solution methods can be used to determine what trajectory a guided wave will take in a plate or other simple or complex geometric object. The solution represented by Equations (5) and (6) is more general than the geodesic equations because it can be applied to digitally defined geometries. An example implementation of an embodiment of the inventive method can be applied to the inspection of a pipeline with an elbow. The flow chart illustrated in FIG. 17 is a flow chart illustrating steps that can be performed to determine the optimum waveguide excitation parameters. The first step 125 can be to collect the geometric parameters of the piping system to be tested. In a simple example case, the geometric parameters of the piping system illustrated in FIGS. 12 and 13 can be obtained. In this example, the diameter of the pipe is 24 inches, the bend radius of the elbow is 1.5 D, and the thickness of the pipe is 0.375 inches. The regions of significance 135 can also be determined. The regions of significance can include information of where the transducer(s) are to be mounted and determining the area of the piping system to be inspected. In this example, the transducer array 606 can be capable of launching a guided wave in any direction desired and can be mounted to the pipe at a location illustrated in FIG. 13. The area to be inspected is represented in this example as the left-most end of the second section of pipe 503.

Reference properties 145 such as dispersion curves can then be calculated by the computer system 450 based on the material properties and geometry of the pipe system. In this example the pipe material is mild steel. An example dispersion curve for this pipe is shown in FIG. 14. Using these calculations the initial position and necessary launch angle 155 required for successful inspection of the region of interest are determined with the computer system 450. The computer system 450 then computes the necessary time delays, phase delays, and or amplitudes 165 to send to the transducer(s) 605 in the transducer array 606 in FIG. 13.

A controller 350 performs the inspection 175 by implementing the data computed in 165 to send the necessary signals to the transducer array 606, records signal reflections and reports the results to the computer system 450 for processing 185. When the processing 185 is finished, the test results 195 are reported.

Figure 12:
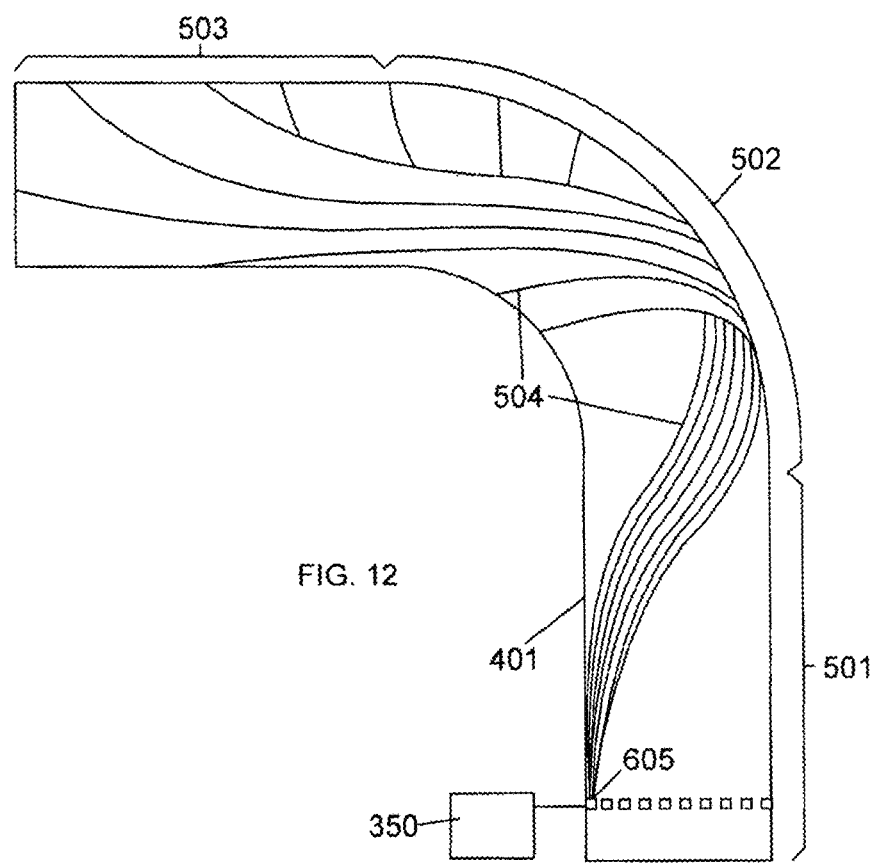
FIGS. 12 and 13 illustrate the top view of a pipe structure undergoing non-destructive wave energy testing.
Figure 15:
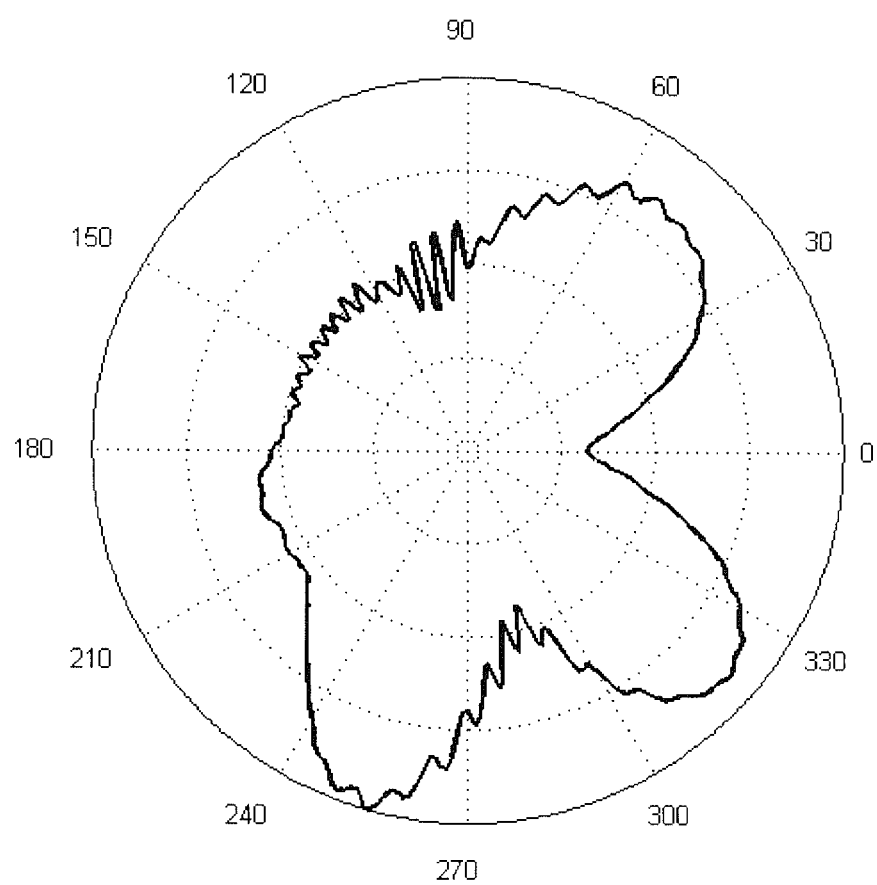
FIGS. 15 and 16 illustrate a graphical representations of insonification energy levels at a region of interest in a waveguide structure.
Figure 16:
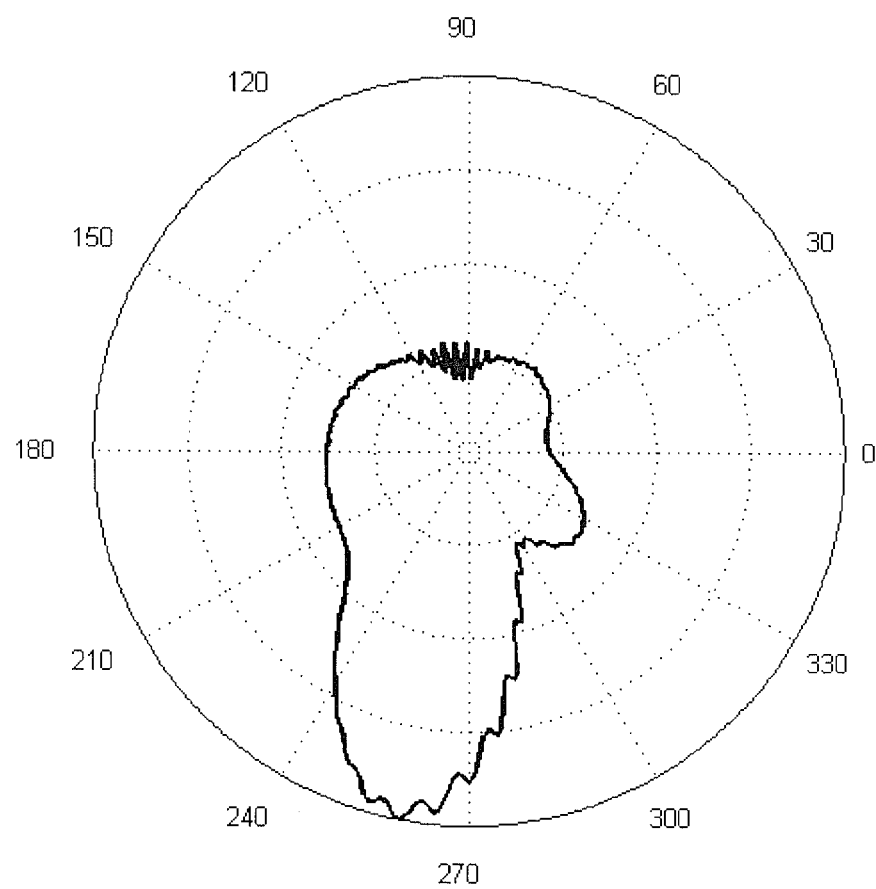

In this example, the computation of the initial conditions 155 can be configured to send guided wave energy to a wide circumferential region of the area of interest, as demonstrated in FIG. 12. The resulting circumferential profile of energy from this example would be as shown in FIG. 15 which illustrates a polar diagram of the relative isonification energy levels around the circumference of the pipe at the left side end. In this example, the isonification energy level is highest at about 30-65 degrees, 235-270 degrees and 300-340 degrees. There are also reduced levels of isonification energy around the remainder of the pipe circumference. In another simple example on the same piping system with the same geometric parameters 125, with the same regions of interest 135, with the same reference properties 145, and the same sensor configuration 606, the computation of the initial conditions 155 could be configured to send guided wave energy to a vary narrow circumferential region of the area of interest. This example is demonstrated in FIG. 13. The resulting circumferential profile of energy from this example would be as shown in FIG. 16. In contrast to the more widespread insonification energy levels illustrated in FIG. 15, in FIG. 16, the insonification level is significant only in a specific region between about 240-275 degrees and all other portions of the circumference have much lower insonification energy. This control of the isonification energy can allow users to perform non-destructive testing on very specific regions of interest in the test structure. An implementation of helical solutions in a pipe having an elbow bend can be illustrated with reference to FIGS. 8-10 which show a set of three wave trajectories 411, 413, 415 which are transmitted through a bent section of pipe 401. Each of the three trajectories 411, 413, 415 begins from a common point, a transducer 405 on the pipe 401 as shown in FIG. 10. However, each of the trajectories has a different starting velocity direction as shown in FIG. 8. These trajectories 411, 413, 415 represent the paths taken by the main portion of a guided wave launched from this position and initially moving in the respective directions of the trajectories. Thus, although the trajectories 411, 413, 415 have the same starting point from a single transducer 405, they diverge along the length of the pipe 401 and move along different circumferential portions of the pipe 401 as shown in FIG. 9. The guided wave energy path may only depend on the geometry of the waveguide, the initial location of the wave, and the initial direction of the wave. Neither the velocity nor the frequency of the wave will affect its propagation path. The geodesics are merely straight lines on the curved surface of the test structure. A wave will tend to move straight ahead (i.e. will follow the geodesic) and the direction that appears to be straight ahead will not be different for two waves of different velocities or frequencies.

Figure 11:
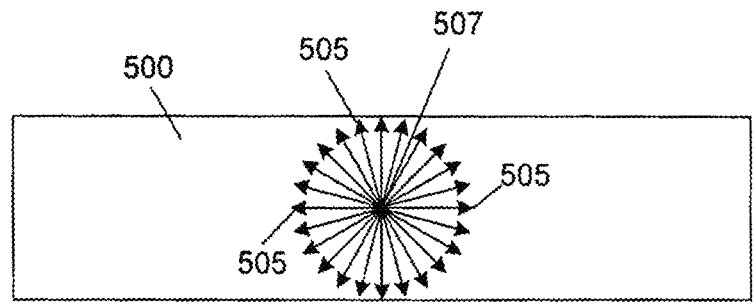
FIG. 11 shows a set of many wave energy trajectories on a pipe structure starting from a common location and propagating in many different directions.

FIG. 11 shows a set of many wave energy trajectories 505 on a pipe structure 500 starting from a common location 507 and propagating in many different directions. By negating the sign of the velocity direction in Equation (4), it is possible to determine the path previously traveled by a guided wave having the solution of interest in the current iteration. This makes it possible to determine where a wave mode has potentially been and can be used to enhance signal processing.

Figure 13:
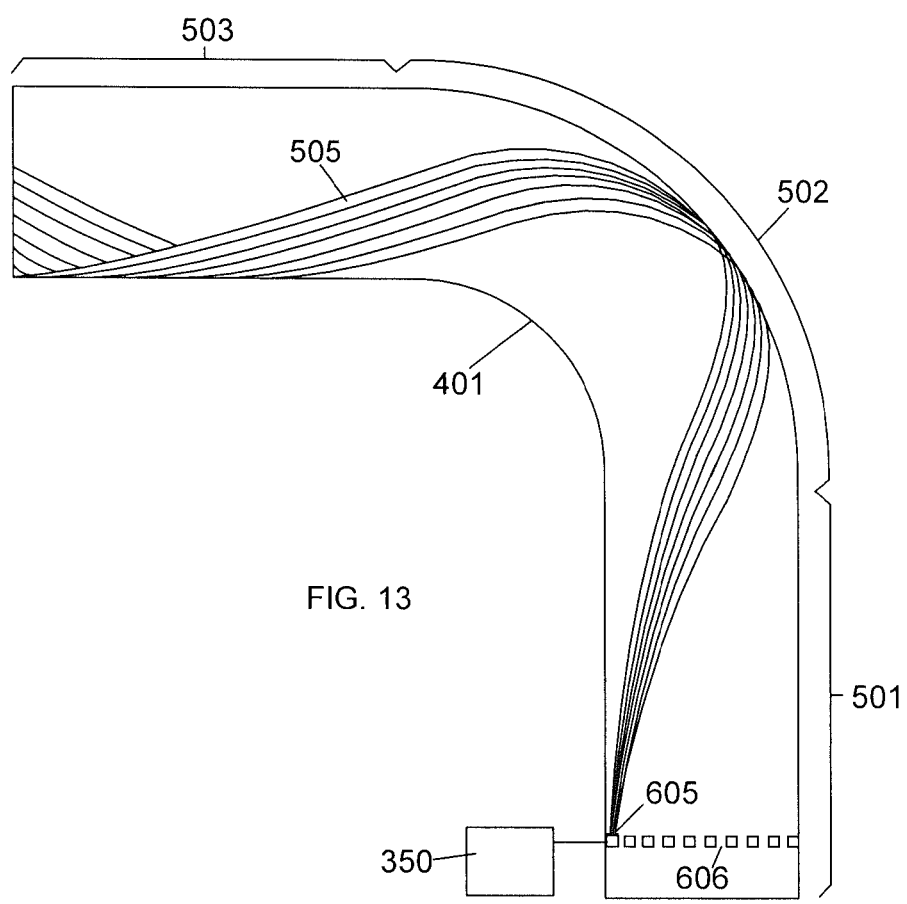

Knowledge of these paths enables a user to deliberately configure the excitation parameters of a guided wave test to direct energy to a particular region of a waveguide to be tested, or along multiple paths to converge at any desired location in a structure with complex or simple geometry, and will be able to purposely focus guided wave energy at an arbitrary point of interest. FIGS. 12 and 13 show examples of the insonified regions of a bent pipe 401 for two sets of wave excitation parameters that are almost identical. In this example, the bent pipe 401 includes a first region 501 on a first side of the bent section 502 and a second section 503 on the opposite side of the bent section 502. In both FIGS. 12 and 13, the excitation transducer 605 is located in the same position and the wave energies 504, 505 are transmitted from this location.

A difference between FIGS. 12 and 13 is that the wave energies are directed to propagate in slightly different initial directions from the excitation transducer 605. The excitation directions of the wave energies 504 illustrated in FIG. 12 are more circumferentially oriented than the initial wave energy 505 directions of FIG. 13. As illustrated, both sets of wave energies 504, 505 remain in close proximity to each other in the first section 501 and maintain uniform insonification regions. However, the difference in the insonified region after the elbow 502 in the second section 503 is very significant. In FIG. 12, the wave energy 504 spreads out after traversing the elbow section 502 to cover a large portion of the straight section of pipe. In contrast, FIG. 13 illustrates the wave energy 505 spreads very little in the second section 503 of pipe 401 directly following the elbow section 502.

These different wave energy patterns can be used for different non-destructive testing applications. The wave energy 504 illustrated in FIG. 12 could be used to quickly screen a large portion of the second section 503 straight pipe beyond the elbow section 502. Any features in the pipe 401 would reflect a signal back towards the first section 501 which could be detected by an array of transducers 606. However, because the wave energy 504 is so spread out, it can be difficult to determine the circumferential location and extent of the feature detected by the wave energy 504 based upon the reflected wave energies.

In contrast, the wave energy 505 illustrated in FIG. 13 could be used to focus guided wave energy 505 on a relatively small portion of the pipe 401 on the second section 503 on the opposite side of the bent elbow section 502. If the narrow wave energy 505 does not contact a defect feature, none of the wave energy will be reflected and the feature may not be detected. However, additional wave energies can be transmitted through different circumferential positions on the pipe 401 so that a sequence of tests can be performed to insonify all regions of the pipe 401. Because the guided waves are focused, the reflected waves can more precisely identify the position of the feature or defect in the pipe 401 based upon the time of flight of the reflected wave energy and the knowledge of where the wave energy has been, as determined by the predicted path of the wave energies. The inventive method allows a user of guided waves to focus guided wave energy as desired on specific regions of interest of waveguides of simple or complex geometry. Of particular relevance is the ability to quickly calculate the parameters needed to focus guided wave energy at arbitrary locations of interest in bent pipes.

In the practice of the inventive system, it will be understood that the methods described herein can be performed using different modes of operation such as torsional, flexural and longitudinal. Different frequency operations are possible for use in the method such as single frequency, multiple frequencies and frequencies across a range of frequencies. Different wave types can also be used including lamb, surface, shear, shear horizontal, shear vertical and longitudinal, and combinations thereof. Among the sensors and transducers that can be used in the practice of the methods described herein are piezo-electric, magnetostrictive, and electromechanical acoustic transducers (EMAT), and combinations thereof.

It will be understood that the inventive system has been described with reference to particular embodiments, however additions, deletions and changes could be made to these embodiments without departing from the scope of the inventive system. Although the systems that have been described include various components, it is well understood that these components and the described configuration can be modified and rearranged in various other configurations.

What is claimed is:

1. A method for guided wave non-destructive testing comprising:
    providing a waveguide structure to be non-destructively tested, the waveguide structure including a bend section such that the waveguide structure's axis or plane of symmetry changes direction, a first section on a first side of the bend section and a second section on a second side of the bend section that is opposite the first side;
    providing at least one ultrasonic guided wave transducer coupled to the first section of the waveguide structure;
    predicting, using a computer employing an algorithm which includes a mathematical representation of the waveguide structure and the computer employing at least one set of initial wave conditions, at least one wave propagation path from the at least one ultrasonic guided wave transducer;
    identifying, using the at least one predicted wave propagation path, at least one set of insonifying initial wave conditions, each at least one set of identified insonifying initial wave conditions being a set of initial wave conditions that corresponds to a predicted wave propagation path from the at least one ultrasonic guided wave transducer to a region of interest in the second section;
    selecting one or more sets of identified insonifying initial wave conditions from the at least one set of identified insonifying initial wave conditions;
    calculating, by the computer using the algorithm, guided wave excitation parameters for insonification of the region of interest within the second section of the waveguide structure with at least one ultrasonic signal from the at least one ultrasonic guided wave transducer on the first section of the waveguide structure, the calculated guided wave excitation parameters being based on the one or more selected sets of identified insonifying initial wave conditions;
    transmitting the at least one ultrasonic signal according to the calculated guided wave excitation parameters from the at least one ultrasonic guided wave transducer through the first section and the bend section to the second section of the waveguide structure; and
    insonifying the region of interest with at least one ultrasonic signal according to the calculated guided wave excitation parameters transmitted by the at least one ultrasonic guided wave transducer.

2. The method of claim 1 further comprising:
    reflecting the at least one ultrasonic signal off of a feature in the second section of the waveguide structure;
    transmitting the at least one ultrasonic signal from the feature in the second section through the bend section and the first section; and
    receiving the at least one ultrasonic signal by the at least one ultrasonic guided wave transducer.

3. The method of claim 2 further comprising:
    analyzing, by the computer or a sensor configuration, the at least one ultrasonic signal received by the at least one ultrasonic guided wave transducer to determine the location and direction of the received signal; and
    determining, by the computer, a trajectory through the waveguide structure followed by the at least one received signal.

4. The method of claim 3 wherein the trajectory through the waveguide structure is used in conjunction with the analysis of the at least one received signal to determine a presence and location of a feature in the waveguide structure.

5. The method of claim 3 wherein a feature of the at least one received signal is determined to be a defect in the second section of the waveguide structure.

6. The method of claim 1 wherein a first ultrasonic signal is transmitted from a first ultrasonic guided wave transducer and a second ultrasonic signal is transmitted from a second ultrasonic guided wave transducer wherein phases of the first ultrasonic signal transmitted from the first ultrasonic guided wave transducer and the second ultrasonic signal transmitted from the second ultrasonic guided wave transducer are not identical.

7. The method of claim 1 wherein a first ultrasonic signal is transmitted from a first ultrasonic guided wave transducer and a second ultrasonic signal is transmitted from a second ultrasonic guided wave transducer and the first ultrasonic signal and the second ultrasonic signal are not transmitted simultaneously.

8. The method of claim 1 wherein a first ultrasonic signal is transmitted from a first ultrasonic guided wave transducer and a second ultrasonic signal is transmitted from a second ultrasonic guided wave transducer and a first amplitude of the first ultrasonic signal and a second amplitude of the second ultrasonic signal are not identical.

9. The method of claim 1 wherein a first ultrasonic signal is transmitted from a first ultrasonic guided wave transducer and a second ultrasonic signal is transmitted from a second ultrasonic guided wave transducer, and the first ultrasonic signal and the second ultrasonic signal reach the region of interest simultaneously during the insonifying of the second section.

10. The method of claim 1 wherein the at least one ultrasonic signal travels in a helical path around the waveguide structure during the transmitting of the at least one ultrasonic signal from the at least one ultrasonic guided wave transducer through the first section and the bend section to the second section of the waveguide structure.

11. The method of claim 1 further comprising:
    confirming, based on the guided wave excitation parameters, that the second section of the waveguide structure has been insonified with the at least one ultrasonic signal corresponding to the guided wave excitation parameters and that the at least one ultrasonic signal has been transmitted by the at least one ultrasonic transducer.

12. The method of claim 1 wherein the insonifying is performed using a wave mode selected from the group consisting of torsional, flexural and longitudinal.

13. The method of claim 1 wherein the at least one ultrasonic signal consists of one or more frequencies from the group consisting of single frequency, multiple frequencies and frequencies across one or more ranges of frequencies.

14. The method of claim 1 wherein the insonifying is performed using one or more wave types selected from the group consisting of lamb, surface, shear, shear horizontal, shear vertical, longitudinal, and combinations thereof.

15. The method of claim 1 wherein the ultrasonic guided wave transducer is of a type selected from the group consisting of piezo-electric, magnetostrictive, electromechanical acoustic, and combinations thereof.

16. The method of claim 1, each at least one set of initial wave conditions being provided by a user or by the computer; and
the selecting one or more selected sets of insonifying wave conditions being performed by the user or by the computer.

17. A method for guided wave non-destructive testing including a region of interest comprising:
providing a waveguide structure not containing a bend section, the waveguide structure is to be non-destructively tested;
providing at least one ultrasonic guided wave transducer coupled to the waveguide structure;
predicting, using a computer employing an algorithm which includes a mathematical representation of the waveguide structure and the computer employing at least one set of initial wave conditions, at least one wave propagation path from the at least one ultrasonic guided wave transducer;
identifying, using the at least one predicted wave propagation path, at least one set of insonifying initial wave conditions, each at least one set of identified insonifying initial wave conditions being a set of initial wave conditions that corresponds to a predicted wave propagation path from the at least one ultrasonic guided wave transducer to the region of interest;
selecting one or more sets of identified insonifying initial wave conditions from the at least one set of identified insonifying initial wave conditions;
calculating, by the computer using the algorithm, guided wave excitation parameters for insonification of the region of interest within the waveguide structure with at least one ultrasonic signal from the at least one ultrasonic guided wave transducer coupled to the waveguide structure, the calculated guided wave excitation parameters being based on the one or more selected sets of identified insonifying initial wave conditions;
transmitting the at least one ultrasonic signal according to the calculated guided wave excitation parameters from the at least one ultrasonic guided wave transducer through the waveguide structure; and
insonifying the region of interest with the at least one ultrasonic signal according to the calculated guided wave excitation parameters transmitted by the at least one ultrasonic guided wave transducer.

18. The method of claim 17 further comprising:
reflecting the at least one ultrasonic signal off of a feature in the waveguide structure;
transmitting the at least one ultrasonic signal from the feature in the waveguide structure; and
receiving the at least one ultrasonic signal by the at least one ultrasonic guided wave transducer.

19. The method of claim 18 further comprising:
analyzing, by the computer or a sensor configuration, the at least one ultrasonic signal received by the at least one ultrasonic guided wave transducer to determine a location and direction of the received at least one ultrasonic signal; and
determining, by the computer, a trajectory through the waveguide structure followed by the received at least one ultrasonic signal.

20. The method of claim 19 wherein the determination of the trajectory of the received at least one ultrasonic signal through the waveguide structure is used in conjunction with an analysis of the received at least one ultrasonic signal by the computer to determine a presence and a location of a feature in the waveguide structure.

21. The method of claim 19 wherein a feature of the received at least one ultrasonic signal is determined to be a defect in the region of interest of the waveguide structure.

22. The method of claim 17 wherein a first ultrasonic signal is transmitted from a first ultrasonic guided wave transducer and a second ultrasonic signal is transmitted from a second ultrasonic guided wave transducer, wherein phases of the first ultrasonic signal transmitted from the first ultrasonic guided wave transducer and the second ultrasonic signal transmitted from the second ultrasonic guided wave transducer are not identical.

23. The method of claim 17 wherein a first ultrasonic signal is transmitted from a first ultrasonic guided wave transducer and a second ultrasonic signal is transmitted from a second ultrasonic guided wave transducer and the first ultrasonic signal and the second ultrasonic signal are not transmitted simultaneously.

24. The method of claim 17 wherein a first ultrasonic signal is transmitted from a first ultrasonic guided wave transducer and a second ultrasonic signal is transmitted from a second ultrasonic guided wave transducer and a first amplitude of the first ultrasonic signal and a second amplitude of the second ultrasonic signal are not identical.

25. The method of claim 17 wherein a first ultrasonic signal is transmitted from a first ultrasonic guided wave transducer and a second ultrasonic signal is transmitted from a second ultrasonic guided wave transducer, and the first ultrasonic signal and the second ultrasonic signal reach a region of interest simultaneously during the insonifying of the waveguide structure.

26. The method of claim 17 wherein the at least one ultrasonic signal travels in a helical path around the waveguide structure during the transmitting of the at least one ultrasonic signal from the at least one ultrasonic guided wave transducer.

27. The method of claim 17 wherein the insonifying is performed using a wave mode selected from the group consisting of torsional, flexural and longitudinal.

28. The method of claim 17 wherein the at least one ultrasonic signal from the at least one ultrasonic guided wave transducer consists of one or more frequencies from the group consisting of single frequency, multiple frequencies and frequencies across one or more ranges of frequencies.

29. The method of claim 17 wherein the insonifying is performed using a wave type selected from the group consisting of lamb, surface, shear, shear horizontal, shear vertical, longitudinal, and combinations thereof.

30. The method of claim 17 wherein the ultrasonic guided wave transducer is of a type selected from the group consisting of piezo-electric, magnetostrictive, electromechanical acoustic, and combinations thereof.

31. The method of claim 17, each at least one set of initial wave conditions being provided by a user or by the computer; and the selecting one or more selected sets of insonifying wave conditions being performed by the user or by the computer.

* * * * *